(12) United States Patent
Cinader, Jr. et al.

(10) Patent No.: US 7,910,632 B2
(45) Date of Patent: Mar. 22, 2011

(54) PACKAGED ORTHODONTIC ASSEMBLY WITH ADHESIVE PRECOATED APPLIANCES

(75) Inventors: David K. Cinader, Jr., Yorba Linda, CA (US); Joan V. Brennan, Sierra Madre, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 614 days.

(21) Appl. No.: 11/422,790

(22) Filed: Jun. 7, 2006

(65) Prior Publication Data

US 2006/0207893 A1  Sep. 21, 2006

Related U.S. Application Data

(62) Division of application No. 10/742,561, filed on Dec. 19, 2003, now abandoned.

(51) Int. Cl.
  *A61K 6/00* (2006.01)
  *A61B 19/02* (2006.01)
  *B65D 83/10* (2006.01)
(52) U.S. Cl. ........... 523/118; 206/63.5; 206/369; 433/9; 433/77; 523/120; 526/277
(58) Field of Classification Search ................. 206/63.5, 206/368, 369, 460; 433/8–11, 24, 26, 77, 433/79; 522/84, 182, 183; 523/118, 120; 526/277
See application file for complete search history.

(56) References Cited

U.S. PATENT DOCUMENTS

| 3,814,717 | A | | 6/1974 | Wilson et al. | |
| 4,719,149 | A | * | 1/1988 | Aasen et al. | 433/226 |
| 4,820,151 | A | | 4/1989 | Pospisil | |
| 4,880,660 | A | * | 11/1989 | Aasen et al. | 433/226 |
| 4,927,362 | A | | 5/1990 | Snead | |
| 4,978,007 | A | | 12/1990 | Jacobs et al. | |
| 5,015,180 | A | | 5/1991 | Randklev | |
| 5,172,809 | A | | 12/1992 | Jacobs et al. | |
| 5,221,202 | A | | 6/1993 | James | |
| 5,328,363 | A | | 7/1994 | Chester et al. | |
| 5,348,154 | A | | 9/1994 | Jacobs et al. | |
| 5,350,059 | A | | 9/1994 | Chester et al. | |
| 5,354,199 | A | | 10/1994 | Jacobs et al. | |
| 5,373,034 | A | * | 12/1994 | Wang et al. | 433/215 |
| 5,429,229 | A | | 7/1995 | Chester et al. | |
| 5,538,129 | A | | 7/1996 | Chester et al. | |

(Continued)

FOREIGN PATENT DOCUMENTS

JP  6-504459  5/1994

(Continued)

OTHER PUBLICATIONS

U.S. Appl. No. 60/494,603.

*Primary Examiner* — Luan K Bui
(74) *Attorney, Agent, or Firm* — Philip P. Soo (57) ABSTRACT

An assembly for use in orthodontic treatment includes at least two articles, and each article includes an orthodontic appliance as well as an adhesive that extends across the base of each appliance. The adhesive of at least one article differs from the adhesive of at least one other article in terms of composition, properties or characteristics, such that the adhesive can be tailored to enhance the bond between the particular selected appliance and its intended tooth.

8 Claims, 4 Drawing Sheets

U.S. PATENT DOCUMENTS

| | | | |
|---|---|---|---|
| 5,552,177 | A | 9/1996 | Jacobs et al. |
| 5,575,645 | A | 11/1996 | Jacobs et al. |
| 5,636,736 | A | 6/1997 | Jacobs et al. |
| 5,692,896 | A * | 12/1997 | Pospisil et al. .................. 206/369 |
| 5,746,594 | A | 5/1998 | Jordan et al. |
| 5,762,192 | A | 6/1998 | Jacobs et al. |
| 5,827,058 | A | 10/1998 | Kelly et al. |
| 5,971,754 | A | 10/1999 | Sondhi et al. |
| 6,050,815 | A | 4/2000 | Adam et al. |
| 6,089,861 | A | 7/2000 | Kelly et al. |
| 6,089,868 | A | 7/2000 | Jordan et al. |
| 6,126,922 | A | 10/2000 | Rozzi et al. |
| 6,183,249 | B1 | 2/2001 | Brennan et al. |
| 6,213,767 | B1 | 4/2001 | Dixon et al. |
| 6,331,080 | B1 | 12/2001 | Cole et al. |
| 6,444,725 | B1 | 9/2002 | Trom et al. |
| 6,512,068 | B1 * | 1/2003 | Nakatsuka .................... 526/277 |
| 6,513,897 | B2 | 2/2003 | Tokie |
| 6,528,555 | B1 | 3/2003 | Nikutowski et al. |
| 6,554,612 | B2 | 4/2003 | Georgakis et al. |
| 6,583,197 | B1 * | 6/2003 | Wada et al. ...................... 522/84 |
| 6,957,957 | B2 | 10/2005 | Pospisil |
| 2001/0055741 | A1 | 12/2001 | Dixon et al. |
| 2002/0037977 | A1* | 3/2002 | Feldstein et al. ................. 526/60 |
| 2003/0134934 | A1* | 7/2003 | Kojima et al. ................. 523/120 |
| 2003/0196914 | A1 | 10/2003 | Tzou et al. |
| 2005/0074716 | A1 | 4/2005 | Cleary et al. |
| 2005/0074717 | A1 | 4/2005 | Cleary et al. |
| 2005/0136370 | A1 | 6/2005 | Brennan et al. |

FOREIGN PATENT DOCUMENTS

| | | |
|---|---|---|
| JP | 2003-532485 | 11/2003 |
| WO | WO 92/08419 | 5/1992 |
| WO | WO 00/69393 | 11/2000 |
| WO | WO 01/85047 | 11/2001 |

* cited by examiner

PACKAGED ORTHODONTIC ASSEMBLY WITH ADHESIVE PRECOATED APPLIANCES

CROSS REFERENCE TO RELATED APPLICATIONS

This application is a divisional application of U.S. Ser. No. 10/742,561, filed Dec. 19, 2003, published as U.S. Publication No. 2005/0133384-A1, now abandoned.

BACKGROUND OF THE INVENTION

1. Field of the Invention

This invention relates to a packaged assembly of orthodontic appliances that are used in the patient's oral cavity during the course of orthodontic treatment. More particularly, the present invention relates to an assembly of orthodontic appliances having a quantity of adhesive that has been applied to the base of each appliance by the manufacturer.

2. Description of the Related Art

Orthodontic treatment involves movement of malpositioned teeth to orthodontically correct positions. Tiny orthodontic appliances known as brackets are connected to exterior surfaces of the patient's teeth, and an archwire is placed in a slot of each bracket. The archwire forms a track to guide movement of the teeth to desired positions for correct occlusion. End sections of the archwire are often received in appliances known as buccal tubes that are fixed to the patient's molar teeth. In recent years it has become common practice to use adhesives to bond orthodontic appliances to the surface of the tooth, using either direct or indirect methods.

For many years, it was common practice to apply orthodontic adhesive to the base of the appliance immediately before the appliance was placed on the tooth. In some instances, a quantity of adhesive was dispensed onto a mixing pad or dispensing well, and a small spatula or other hand instrument was then used to apply a small dab of adhesive to each appliance. In other instances, a quantity of adhesive was dispensed from a syringe directly onto the base of the appliance.

Adhesive precoated brackets are known and offer significant advantages to the orthodontist. Adhesive precoated brackets have a bonding base upon which the manufacturer may apply a precise quantity of adhesive such as a photocurable adhesive. In direct bonding methods, when it is desired to mount the bracket on a tooth, the bracket is simply removed from the package and placed directly onto the tooth. For indirect bonding methods, brackets are removed from the package and placed, for example, on a replica plaster or "stone" model of the patient's dental arch to provide a custom base for later mounting on the patient's tooth, commonly using a transfer tray.

In addition to good handling properties and adequate adhesion, practitioners often desire that photocurable adhesives provide other desirable functional properties, including, for example, sustained fluoride release. In many applications, it is also desirable that the adhesive have adequate hydrophilicity or moisture tolerance, as indicated, for example, by the ability of the adhesive to absorb water or saliva, and/or the ability to provide an adequate bond under moist conditions.

Adhesive precoated brackets are typically packaged in containers that protect the adhesive from light, moisture and contaminants. Known containers include containers that receive only a single bracket. Optionally, the containers are received in a holder that is constructed for a single patient, and the holder carries a sufficient number of containers with their contained appliance for all or substantially all of the patient's teeth that are undergoing orthodontic treatment.

Over the years, many attempts have been made to improve bonding materials for orthodontic appliances to help ensure that the appliances do not unintentionally detach from the teeth. If, for example, an appliance debonds from the tooth during the course of treatment, the patient must return to the practitioner's office for reattachment or replacement of the appliance so that treatment can resume. Obviously, such occurrences represent a nuisance for both the practitioner and the patient, and may also increase the treatment cost as well as the length of time needed for treatment.

SUMMARY OF THE INVENTION

The present invention is directed toward a packaged assembly of orthodontic appliances having an adhesive extending across the base of the appliances. The adhesive associated with at least one of the appliances differs in at least one property from the adhesive that is associated with at least one other appliance. As examples, the adhesives may vary by composition and/or by characteristics. Aspects of the adhesive that may vary might include one or more of the following: proportion of compositional elements, identity of compositional elements, bond strength after hardening, curing agents or curing mechanisms, hydrophilicity, color before hardening, color after hardening, the change of color after hardening, viscosity before hardening, translucency after hardening, tack before hardening, and, if multilayered, the number of layers, patterns of layers, thickness of layers, and composition of layers.

The present invention is a significant advantage, in that the properties of the adhesive of each appliance may be tailored to help optimize bonding to different teeth in the oral cavity. For example, the adhesive associated with appliances for the posterior teeth may be softer or less viscous than the adhesive associated with appliances intended for the anterior teeth. Such an assembly may be preferred by some practitioners, since the posterior appliances often have a larger base than anterior appliances and consequently provide more resistance to firmly seating the base of the appliance against the tooth surface. Other examples are also possible.

In more detail, the present invention is directed to a packaged orthodontic assembly comprising at least two articles. Each article includes an orthodontic appliance having a base for connection to a tooth of an orthodontic patient. Each article also includes an adhesive extending across at least a portion of the base of the corresponding appliance. The adhesive of at least one of the articles differs from the adhesive of at least one other article.

The invention in its various embodiments is described in more detail below and is illustrated in the accompanying drawings.

DEFINITIONS

As used herein, "orthodontic appliance" refers to any device intended to be bonded to a tooth structure, including, but not limited to, orthodontic brackets, buccal tubes, bite openers, buttons, and cleats. Thus, the term "orthodontic appliance" encompasses orthodontic bands. The appliance has a base for receiving adhesive and it can be a flange made of metal, plastic, ceramic, and combinations thereof. Alternatively, the base can be a custom base formed from cured adhesive layer(s) (i.e., single or multi-layer adhesives).

As used herein, a "release" substrate refers to a substrate in contact with an article that is removed from the article before or during use of the article.

As used herein, a "multi-layer" adhesive refers to an adhesive having two or more layers.

As used herein, a "layer" refers to a discontinuous (e.g., a patterned layer) or continuous (e.g., non-patterned) material extending across all or a portion of a different material. A layer may be of uniform or varying thickness.

As used herein, a "patterned layer" refers to a discontinuous layer in which the material of the patterned layer extends across only selected portions of another material.

As used herein, a "non-patterned layer" refers to a continuous layer in which the material of the non-patterned layer extends across an entire portion of another material.

In general, a layer "extending across" or "attached to" another layer is intended to be broadly interpreted to optionally include one or more additional layers between the two layers.

As used herein, "hardenable" is descriptive of a material that can be cured or solidified, for example, by heating to remove solvent, heating to cause polymerization, chemical cross-linking, radiation-induced polymerization, or crosslinking.

As used herein, "hardener" means a system that initiates hardening of a resin. A hardener may include, for example, a polymerization initiator.

As used herein, "photobleachable" refers to loss of color upon exposure to actinic radiation.

As used herein, "filler" means a particulate material (e.g., an inorganic oxide) in dry powder form capable of being dispersed in a resin. For example, a dental composite preferably includes a powder dispersed in a resin.

As used herein, the term "(meth)acrylate" is a shorthand reference to acrylate, methacrylate, or combinations thereof, and "(meth)acrylic" is a shorthand reference to acrylic, methacrylic, or combinations thereof.

As used herein, the chemical term "group" allows for substitution.

As used herein, "a" or "an" means one or more.

DETAILED DESCRIPTION OF THE PREFERRED EMBODIMENTS

Figure 1:
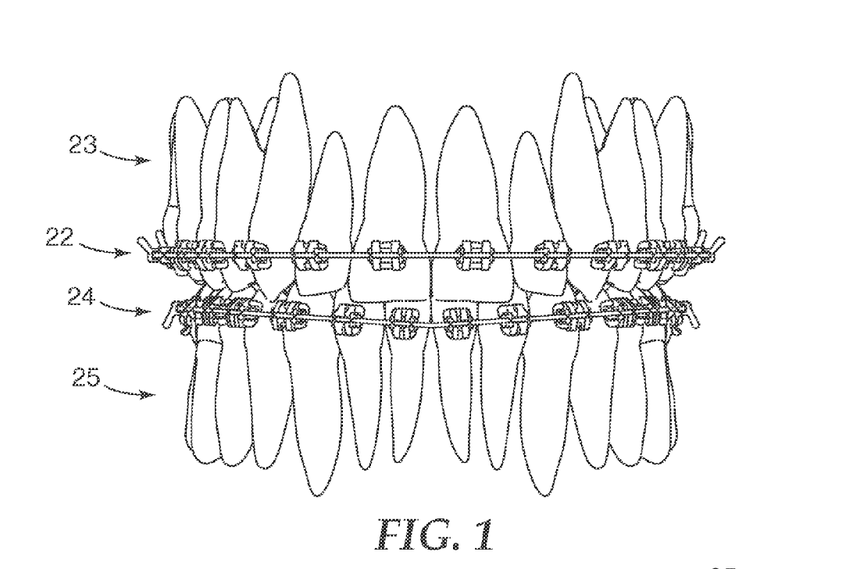
FIG. 1 is a front elevational view showing the teeth of an exemplary patient undergoing orthodontic treatment, wherein orthodontic appliances are affixed to the teeth of the upper and lower jaw and an archwire has been connected to the appliances associated with each jaw.

FIG. 1 illustrates an example of an oral cavity of an orthodontic patient that is undertaking orthodontic therapy. The patient has a first orthodontic brace 22 that is connected to the teeth of the upper dental arch 23 and a lower orthodontic brace 24 that is connected to the teeth of the lower dental arch 25. Each brace 22, 24 includes a set of orthodontic appliances along with an archwire that is received in slots of the appliances, as will be described in more detail below.

Figure 2:
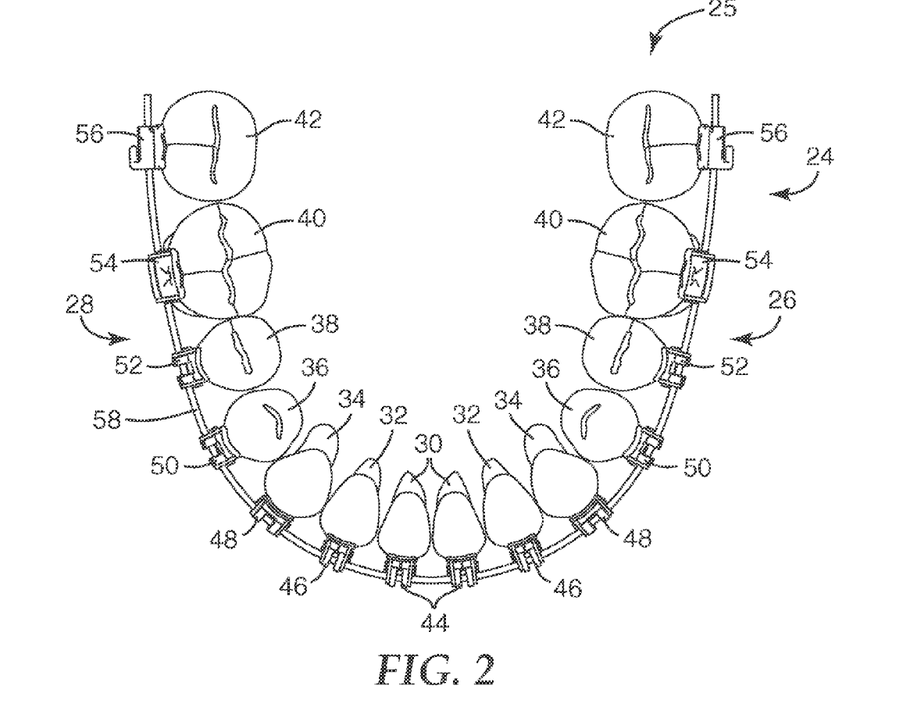
FIG. 2 is an enlarged plan view of the teeth of the lower jaw of the oral cavity illustrated in FIG. 1, also showing the appliances and the associated archwire.

FIG. 2 is an enlarged view of the lower dental arch 25 along with the lower brace 24, looking in a downwardly direction toward the outer or occlusal tips of the teeth. The lower dental arch 25 includes a left quadrant 26 and a right quadrant 28. Each of the quadrants 26, 28 includes a central incisor tooth 30, a lateral incisor tooth 32, a cuspid tooth 34, a first bicuspid tooth 36 and a second bicuspid tooth 38. In addition, each of the quadrants 26, 28 includes a first molar tooth 40 and a second molar tooth 42.

The illustration of the lower dental arch 25 shown in FIG. 2 is only one example of dentition, and many variations are possible. For example, the patient may lack one or more of the illustrated teeth, as may occur in adolescent patients when some of the permanent teeth have not yet erupted. Alternatively, one or more teeth may have been removed prior to orthodontic treatment in order to reduce crowding, especially in instances where the overall size of the dental arch is relatively small. Moreover, the lower dental arch 25 may include third molar teeth, also known as wisdom teeth, which are not illustrated in the drawing.

The lower brace 24 includes a set of appliances connected to the teeth of the lower quadrants 26, 28. In particular, the lower brace 24 in each of the lower quadrants 26, 28 includes a central incisor appliance 44 that is coupled to the central incisor tooth 30, a lateral incisor appliance 46 that is connected to the lateral incisor tooth 32 and a cuspid appliance 48 that is connected to the cuspid tooth 34. The lower brace 24 also includes, along each quadrant 26, 28, a first bicuspid appliance 50 that is coupled to the first bicuspid tooth 36, a second bicuspid appliance 52 that is connected to the second bicuspid tooth 38, a first molar appliance 54 that is connected to the first molar tooth 40 and a second molar appliance 56 that is connected to the second molar tooth 42.

Optionally, one or more of the appliances described above may be omitted in accordance with the preference of the orthodontist. For example, if the second molar teeth 56 have not yet fully erupted, the orthodontist may elect to omit the second molar appliances 56, at least during the early stages of treatment. As another option, the central incisor appliances 44 and the lateral incisor appliances 46 may be identical and instead called "lower anterior appliances".

The lower brace 24 also includes an archwire 58 made of a resilient material. Suitable materials include, for example, metallic materials such as alloys of nitinol and stainless steel. The archwire 58 has a generally overall "U"-shaped configuration and extends along both of the quadrants 26, 28.

Figures 3, 4, 5:
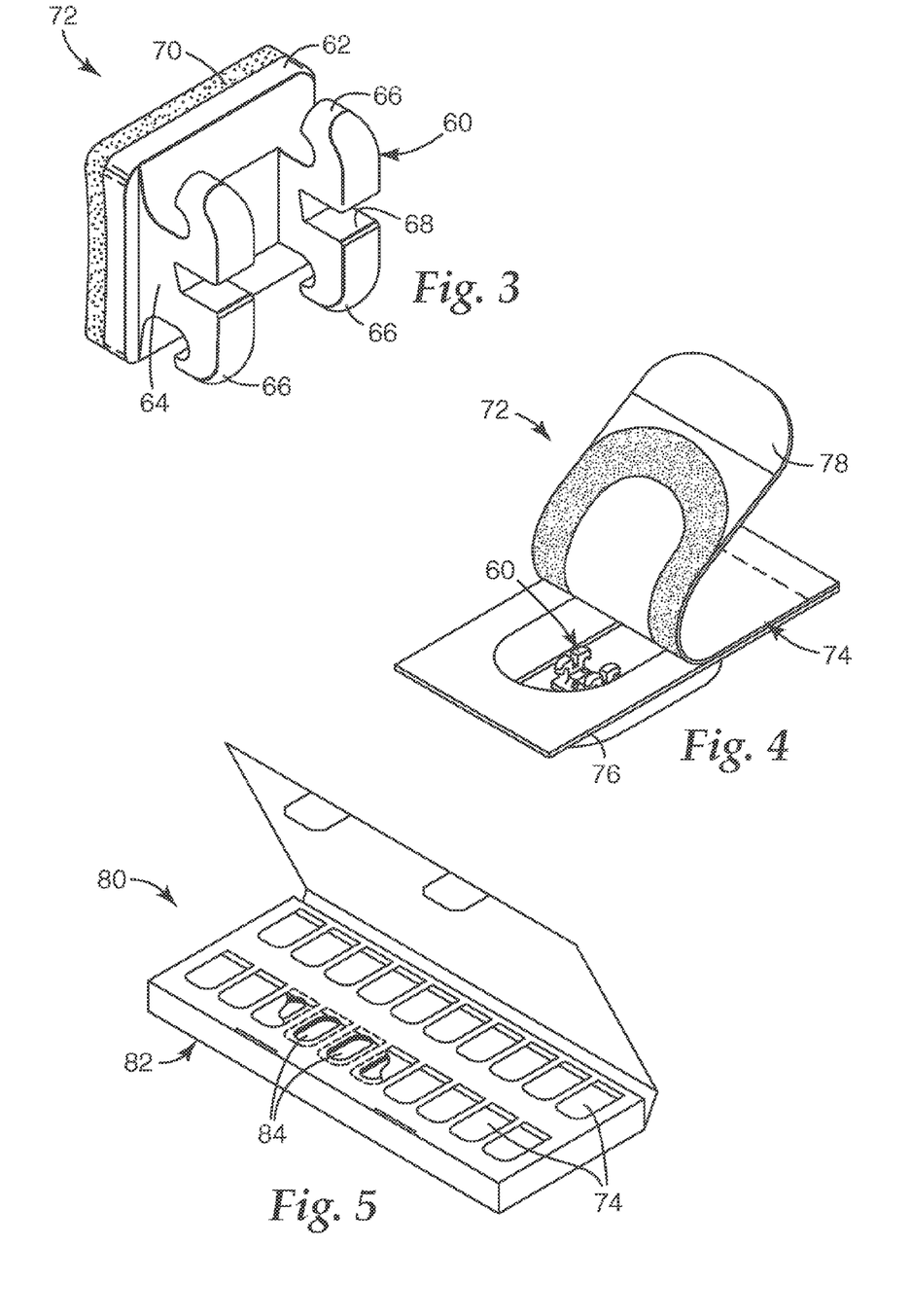
FIG. 3 is an enlarged perspective view of one of the appliances shown in FIG. 2 along with a quantity of an adhesive for bonding the appliance to a tooth surface.
FIG. 4 is a reduced-size illustration of the appliance shown in FIG. 3 along with a container provided for shipping, storing and handling the appliance before use.
FIG. 5 is a packaged orthodontic assembly according to one embodiment of the present invention, which includes a number of containers and appliances such as shown in FIG. 4.

A representative example of an appliance is the appliance 60 that is shown in enlarged view in FIG. 3. The appliance 60 includes a base 62. The appliance 60 also has a body 64 that extends outwardly from the base 62. Base 62 can be a flange made of metal, plastic, ceramic, and combinations thereof. Optionally, the base 62 can be a custom base having an outer surface formed from cured adhesive layer(s) (i.e., single or multi-layer adhesives). Tiewings 66 are connected to the body 64, and an archwire slot 68 extends through a space between the tiewings 66. The base 62, the body 64, and tiewings 66 may be made of any one of a number of materials suitable for use in the oral cavity and having sufficient strength to withstand the correction forces applied during treatment. Suitable materials include, for example, metallic materials (such as stainless steel), ceramic materials (such as monocrystalline or polycrystalline alumina), and plastic materials (such as fiber-reinforced polycarbonate). Optionally, the base 62, the body 64, and the tiewings 66 are integrally made as a unitary component.

An adhesive 70 extends across the base 62 of the appliance 60. The adhesive 70 serves in whole or at least in part to securely fix the appliance 60 to the patient's tooth by a bond having sufficient strength to resist unintended detachment from the tooth during the course of treatment. Preferably, the adhesive 70 is applied to the base 62 of the appliance 60 by the manufacturer. The appliance 60 and that adhesive 70 are collectively referred to as an article 72.

The adhesive may be a liquid, a paste, or a solid material that is converted into a liquid or paste during the bonding procedure. Suitable compositions include composites, compomers, glass ionomers and resin-modified glass ionomers. Examples of light-curable adhesives include Transbond XT brand and Transbond LR brand adhesives from 3M Unitek. Examples of chemical curing adhesives include Sondhi brand Rapid-Set indirect bonding adhesive, Unite brand adhesive, and Concise brand adhesive from 3M Unitek. An example of an adhesive that is both a light-curable adhesive and a chemical curing adhesive is Multi-Cure brand glass ionomer cement from 3M Unitek.

Compositions useful for the adhesive 70 of the present invention are well known to one of skill in the art. Useful compositions include, for example, both light cure and chemical cure orthodontic adhesives. In some embodiments, the compositions are preferably fluoride releasing adhesives, self-etching adhesives, self-priming adhesives, color-changing adhesives, and combinations thereof.

Optionally, the adhesive 70 falls in one of the following classes in accordance with the practitioner's preferences for tooth treatment:

Class I: An adhesive that requires both etching of tooth enamel (using, for example, phosphoric acid or a bisphosphonic acid) and a separate application of a primer to the tooth enamel.

Class II: An adhesive that requires etching (using, for example, phosphoric acid, a bisphosphonic acid or self-etching primer) but not a separate application of primer.

Class III: An adhesive that requires no treatment of the teeth other than cleaning.

Possible primers for use with class I adhesives include orthodontic primers such as Transbond MIP brand primer and Transbond XT brand primer from 3M Unitek and Ortho Solo brand primer from Ormco Corporation. Optionally, the primer may include a photobleachable dye to ensure adequate coverage of the primer on the teeth, a small amount of fluoroalumina silicate glass ("FAS" glass) for providing fluoride release during treatment, a small amount of fumed silica for rheology control purposes, and/or a small amount of silanated quartz filler for enhanced fracture toughness.

Suitable class II adhesives include the adhesives mentioned above. If the adhesive is a multi-layer adhesive, the adhesive may include a layer of primer that first contacts the tooth during a bonding procedure. The primer may be self-etching or non-self-etching. An example of a suitable self-etching primer is Transbond Plus SEP brand primer from 3M Unitek. Optionally, the self-etching primer could incorporate the optional features described above for the class I adhesive.

Suitable class III adhesives avoid the need for etching and priming the teeth and may be referred to as "self-adhesive" compositions. With these adhesives, the practitioner need only clean the teeth prior to application of the dental appliance in a typical bonding procedure. Suitable class III adhesives may include an acid component selected from a methacrylate phosphate (e.g., mono-HEMA phosphate, di-HEMA phosphate, glycerol dimethacrylate (GDMA) phosphate), a solution of a bisphosphonic acid in water or other solvent, and a bisphosphonic acid in powder form (using water for ionizing that is left on the teeth after tooth prophy and rinse). Other class III adhesives may include an ethylenically unsaturated component with acid functionality, an ethylenically unsaturated component without acid functionality, an initiator system, and a filler. Optionally a class III adhesive may be essentially free of water. Examples of class III adhesives have been previously described, e.g. in pending U.S. Provisional Pat. Application No. 60/494,603 filed Aug. 12, 2003.

The class III adhesives described above can optionally incorporate fillers (e.g., a glass ionomer-type filler that binds the water in the usual glass ionomer setting reaction). In addition, any of the class III adhesives described above may incorporate the optional features described in connection with class I adhesives.

Adhesives useful in the present invention may optionally include components such as fluoride releasing agents as described, for example, in U.S. Pat. No. 3,814,717 (Wilson et al.) and U.S. Pat. No. 6,126,922 (Rozzi et al.); adhesive enhancing agents (e.g., titanites, zirconates) as disclosed, for example, in PCT International Publication No. WO 00/69393 (Brennan et al.); fillers; micro fillers; enzyme releasing agents; rheology enhancing agents; photobleachable dyes; and combinations thereof.

In some embodiments, the adhesive 70 of the present invention preferably has an initial color remarkably different than dental structures. Color is preferably imparted to the composition through the use of a photobleachable dye. The composition preferably includes at least 0.001% by weight photobleachable dye, and more preferably at least 0.002% by weight photobleachable dye, based on the total weight of the composition. The composition preferably includes at most 1% by weight photobleachable dye, and more preferably at most 0.1% by weight photobleachable dye, based on the total weight of the composition. The amount of photobleachable dye may vary depending on its extinction coefficient, the ability of the human eye to discern the initial color, and the desired color change.

The color formation and bleaching characteristics of the photobleachable dye varies depending on a variety of factors including, for example, acid strength, dielectric constant, polarity, amount of oxygen, and moisture content in the atmosphere. However, the bleaching properties of the dye can be readily determined by irradiating the composition and evaluating the change in color. Preferably, at least one photobleachable dye is at least partially soluble in a hardenable resin.

Exemplary classes of photobleachable dyes are disclosed, for example, in U.S. Pat. No. 6,331,080 (Cole et al.), U.S. Pat.

No. 6,444,725 (Trom et al.), and U.S. Pat. No. 6,528,555 (Nikutowski et al.). Preferred dyes include, for example, Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein, and combinations thereof.

The color change in the adhesive 70 is initiated by light. Preferably, the color change is initiated using actinic radiation using, for example, a dental curing light which emits visible or near infrared (IR) light for a sufficient amount of time. The mechanism that initiates the color change in the compositions of the invention may be separate from or substantially simultaneous with the hardening mechanism that hardens the resin. For example, a composition may harden when polymerization is initiated chemically (e.g., redox initiation) or thermally, and the color change from an initial color to a final color may occur subsequent to the hardening process upon exposure to actinic radiation.

The change in composition color from an initial color to a final color is preferably quantified by a Color Test as described below. Using the Color Test, a value of $\Delta E^*$ is determined, which indicates the total color change in a 3-dimensional color space. The human eye can detect a color change of approximately 3 $\Delta E^*$ units in normal lighting conditions. The dental composition of the present invention is preferably capable of having a color change, $\Delta E^*$, of at least 10; more preferably, $\Delta E^*$ is at least 15; most preferably $\Delta E^*$ is at least 20.

A useful method for applying adhesive to an orthodontic appliance includes, for example, using automated fluid dispensing systems such as those available under the trade designation AUTOMOVE from Asymtek (Carlsbad, Calif.). Such automated fluid dispensing systems are useful for dispensing both patterned and non-patterned layers. Other useful systems include, for example, piston dispensing systems and multiple resolution fluid applicators as described, for example, in U.S. Pat. No. 6,513,897 (Tokie).

Once the adhesive 70 has been applied to the orthodontic appliance 60, the article 72 can conveniently be packaged in a container. Exemplary containers are well known in the art and are disclosed, for example, in U.S. Pat. No. 5,172,809 (Jacobs et al.) and U.S. Pat. No. 6,089,861 (Kelly et al.).

Referring to FIG. 4, an exemplary embodiment of an article 72 including orthodontic appliance 60 having the adhesive coated on the base thereof is shown. In this embodiment, the article 72 is received in a package 74 that includes a container 76 and cover 78. Cover 78, which is releasably connected to container 76 as initially provided, is peeled from container 76 to open the package for removal of orthodontic appliance 60. In FIG. 4, cover 78 has been peeled back from container 76 to partially open package 74.

In preferred embodiments, the package 74 provides excellent protection against degradation of the adhesive (e.g., photocurable material), even after extended periods of time. Such packages are particularly useful for protecting dyes that impart a color-changing feature to the adhesive. Such packages preferably effectively block the passage of actinic radiation over a broad spectral range, and as a result, the adhesive does not prematurely lose color during storage.

In preferred embodiments, the container 76 comprises a polymer and metallic particles. As an example, container 76 may be made of polypropylene that is compounded with aluminum filler or receives an aluminum powder coating as disclosed, for example, in U.S. Pat. Application Publication No. 2003/0196914 A1 (Tzou et al.). The combination of polymer and metallic particles provides a highly effective block to the passage of actinic radiation to color changing dyes, even though such dyes are known to be highly sensitive to light. Such containers also exhibit good vapor barrier properties. As a result, the rheological characteristics of the adhesive are less likely to change over extended periods of time. For example, the improved vapor barrier properties of such containers provide substantial protection against degradation of the handling characteristics of adhesives so that the adhesives do not prematurely cure or dry or become otherwise unsatisfactory. Suitable covers 78 for such containers can be made of any material that is substantially opaque to the transmission of actinic radiation so that the adhesive does not prematurely cure. Examples of suitable materials for cover 78 include laminates of aluminum foil and polymers. For example, the laminate may comprise a layer of polyethylene-terephthalate, adhesive, aluminum foil, adhesive and oriented polypropylene. Examples of other suitable materials for the container 76 and the cover 78 are described in U.S. Pat. Nos. 4,978,007, 5,328,363, 5,575,645 and 5,636,736.

In some embodiments, the package 74 may include a release substrate as described, for example, in U.S. Pat. No. 6,183,249 (Brennan et al.).

In other embodiments, the package 74 may not include a release substrate. In one embodiment, the package includes a substrate with at least one recess with an interior surface. The package includes a means for positioning the orthodontic appliance inside the recess such that the adhesive layer does not separate from the appliance upon removal of the appliance from the recess. Preferably, the package further includes a cover for the recess and a means for maintaining the cover in contact with the substrate, wherein the means for positioning the orthodontic appliance includes means suspending the appliance in the recess such that the adhesive layer does not contact the interior surface of the recess. Such packages are disclosed, for example, in U.S. Pat. No. 5,172,809 (Jacobs et al.).

In another embodiment, the package includes a carrier having a pair of arms extending toward each other. Each of the arms has an outer end section, with the outer end sections being spaced apart from each other and presenting a channel therebetween. The orthodontic appliance is located in the channel and is supported by the arms with one of the outer end sections extending into an occlusal recess beneath occlusal tiewings of the appliance and the other of the outer end sections extending into a gingival recess beneath gingival tiewings of the appliance. Such orthodontic appliances and packages are described, for example, in U.S. Pat. No. 6,089,861 (Kelly et al.).

The appliances 44-52 are somewhat similar to the appliance 60, and consequently a detailed description of the similar features need not be repeated. Preferably, however, certain other features of each appliance are modified or adapted to better function with the associated teeth. For example, the curvature of the base is preferably changed to match the curvature of the corresponding tooth. Additionally, the overall width of the appliance in a mesial-distal direction may be increased or decreased in corresponding relationship to the width of the associated tooth. Furthermore, each appliance may be constructed with torque and angulation values that are appropriate for the corresponding tooth for the proposed treatment plan.

Optionally, the first molar appliance 54 and the second molar appliance 56 are somewhat similar to the appliances 44-52 described above. As another option, one or both of the molar appliances 54, 56 are similar to the appliances described in applicant's pending U.S. Pat. No. 6,957,957 (Pospisil). As yet another option, one or both of the molar appliances 54, 56 may comprise appliances known as buccal tubes, such as the buccal tube appliances described in U.S. Pat. Nos. 4,820,151 and 4,927,362.

FIG. 5 illustrates a packaged orthodontic assembly 80 according to one embodiment of the invention. The assembly 80 includes a holder 82 having a plurality of receptacles 84. Each of the receptacles 84 receives a package, such as the package 74 described above.

Preferably, the holder 82 has a sufficient number of receptacles 84 and a sufficient number of packages 74 in the receptacles 84 so that an appliance (such as appliance 60) is provided for each of the patient's teeth undergoing treatment. For example, the holder 82 may contain receptacles 84 for each tooth of the upper and lower jaw, including the molar teeth. As another option, the holder 82 may be provided with a smaller number of receptacles 84, such as ten receptacles 84 for the non-molar teeth of the patient's upper jaw and/or ten receptacles 84 for the non-molar teeth of the patient's lower jaw.

Examples of suitable holders are described in more detail in U.S. Pat. Nos. 5,575,645, 5,762,192 and 6,089,861.

In the assembly 80, the adhesive (such as adhesive 70) associated with at least two of the appliances differs or varies. As examples, the composition and/or characteristic(s) of the adhesive may vary. Examples of assemblies where the characteristics vary in two or more articles include assemblies where the viscosity, the refractive index, the translucency, the bond strength and/or the curing mechanism of the adhesive vary. Other suitable examples with differing characteristics include assemblies where the color change of the adhesive upon hardening may vary from one article to another, where the curing mechanism of the adhesive may vary from one article to another and/or where the adhesive may have a varying number of layers from one article to another.

As an example, the assembly 80 may include a first set of articles 72 and a second set of articles 72. Each appliance of the articles 72 of the first set is a posterior appliance for posterior teeth of the dental arch (i.e., the molar teeth and the bicuspid teeth). Each appliance of each article 72 of the second set is an anterior appliance for anterior teeth of the patient's dental arch (i.e., the cuspid teeth, the lateral teeth and the central teeth). The first and second set may include articles for the upper jaw, the lower jaw or both jaws. The adhesive of at least one article of the first set varies from the adhesive of at least one article of the second set.

For instance, the practitioner may prefer a softer or less viscous adhesive in the articles 72 of the first set in comparison to the softness or viscosity of the articles of the second set. Often, the appliances for the posterior teeth have a base with a larger area than the base of appliances intended for use with anterior teeth. The adhesive associated with the posterior appliances, being less viscous, provides less resistance to movement as the bracket is urged into a position firmly seated against the patient's tooth enamel as compared to movement of the anterior appliances. Consequently, such an assembly is beneficial in that the pressure needed for seating the posterior appliances can be adjusted to match the pressure needed for seating the anterior appliances.

Preferably, the viscosity of the adhesive associated with the first set of articles is less than the viscosity of the adhesive associated with the second set of articles. For instance, the viscosity of the adhesive associated with the first set of articles may be about 20% to about 40% less than the viscosity of the adhesive associated with the second set of articles.

More preferably, four sets of articles are provided. The first set of articles includes appliances with a relatively large base for upper first molar teeth. The second set of articles includes appliances for the upper second bicuspid teeth, the lower second bicuspid teeth, the upper second molar teeth and the lower second molar teeth. The third set of articles includes appliances for the upper central teeth, and the upper and lower cuspid teeth. The fourth set of articles includes appliances for the lower central teeth, the upper and lower lateral teeth, and the upper and lower first bicuspid teeth. In this example, the viscosity of the adhesive associated with the first set of articles is in the range of about 60% to about 75% less than the viscosity of the adhesive associated with the fourth set of articles. The viscosity of the adhesive associated with the second set of articles is in the range of about 20% to about 40% less than the viscosity of the adhesive associated with the fourth set of articles, and the viscosity of the adhesive associated with the third set of articles is in the range of about 10% to about 20% less than the viscosity of the adhesive associated with the fourth set of articles.

As yet another example, the viscosity varies with each appliance so that the effort to seat the appliance remains the same from tooth to tooth. For instance, the viscosity may differ according to the following table for appliances with a base having an area as shown:

TABLE

| Appliance | Area (sq in.) | Area (sq mm.) | Viscosity Change |
|---|---|---|---|
| Lower Anterior | 0.0145 | 9.35 | 0% |
| Upper Lateral | 0.0147 | 9.48 | −1% |
| Upper First Bi | 0.0152 | 9.80 | −5% |
| Lower First Bi | 0.0152 | 9.80 | −5% |
| Upper First Molar (small) | 0.016 | 10.32 | −9% |
| Lower First Molar (small) | 0.016 | 10.32 | −9% |
| Upper Central | 0.0168 | 10.84 | −14% |
| Lower Cuspid | 0.0168 | 10.84 | −14% |
| Upper Cuspid | 0.017 | 10.97 | −15% |
| Upper Second Bi | 0.0199 | 12.84 | −27% |
| Lower Second Bi | 0.0199 | 12.84 | −27% |
| Upper Second Molar | 0.0216 | 13.94 | −33% |
| Lower Second Molar | 0.0216 | 13.94 | −33% |
| Upper First Molar (medium) | 0.0224 | 14.45 | −35% |
| Upper First Molar (medium) | 0.0224 | 14.45 | −35% |
| Upper First Molar (large) | 0.0444 | 28.65 | −67% |
| Lower First Molar (large) | 0.0444 | 28.65 | −67% |

As another example, the adhesive associated with the articles of the first set may have a color change during hardening that is greater than the color change during hardening of the adhesive associated with the articles of the second set. Such construction is an advantage in that the adhesive in contact with the posterior teeth is more difficult to see in the oral cavity than the adhesive in contact with the anterior teeth. For instance, the adhesive of the articles of the first set may have a color change, $\Delta E^*$, that is at least 15 percent greater than the color change, $\Delta E^*$, of the adhesive of the articles of the first set.

As yet another example, the adhesive associated with the articles of the first set may have a different color or appearance when hardened in comparison to the color of the hardened adhesive of the articles of the second set. For instance, the adhesive may have a color to match the patient's teeth, and the patient's posterior teeth may be darker in appearance than the patient's anterior teeth. Consequently, in this instance the adhesive in the articles of the first set will be darker than the adhesive in the articles of the second set. This example may be carried out, for example, by providing a greater amount of dye or pigment in the adhesive of the articles of the first set in comparison to the amount of dye or pigment in the adhesive of the articles of the second set.

As another example, the adhesive associated with each article may be selected to match the color of the corresponding tooth. In this example, each article may represent a separate set, and the adhesive may vary from one set to the next in accordance with the color of the tooth. Such an assembly is particularly beneficial for appliances that are transparent or translucent, and/or transmit sufficient light to take on the color of the underlying tooth. Examples of such appliances include appliances made of polycrystalline or single crystal alumina or other ceramic materials, and appliances made of plastic material such as polycarbonate.

As still another example, the adhesive in the articles of the first set may be more hydrophilic than the adhesive of the articles of the second set. Oftentimes, posterior regions of the patient's oral cavity contain a larger quantity of saliva during a bonding procedure than anterior regions. The greater moisture tolerance provided in the adhesive associated with the posterior appliances helps to ensure that the strength of the resulting bond is not unduly compromised in instances where significant moisture is present.

In another embodiment, the packaged orthodontic assembly includes a first set of articles associated with the patient's lower jaw and a second set of articles associated with the patient's upper jaw. For example, the practitioner may prefer to use light-transmissive orthodontic appliances such as ceramic brackets on the upper teeth, and use less expensive metallic brackets on the patient's lower teeth where the appliances are less noticeable. In that instance, the adhesive associated with the appliances of the upper teeth may be tailored to provide enhanced bonding for ceramic appliances, while the adhesive associated with the metallic appliances may be tailored to provide enhanced bonding for metallic appliances. As an example, the adhesive associated with the ceramic appliances may have an index of refraction that matches the index of refraction of the ceramic material so that it is difficult to see, while the adhesive associated with the metallic appliances may have a different index of refraction since it is substantially covered by the appliance and less noticeable during the course of treatment.

In another embodiment, the orthodontic assembly has a first set of articles for the patient's upper central and lateral teeth, and a second set of articles for the patient's lower central and lateral teeth. The assembly also includes a third set of articles for the patient's upper cuspid, bicuspid and molar teeth, and a fourth set of articles for the patient's lower cuspid, bicuspid and molar teeth. In this example, the bond strength of the adhesive associated with the second set of articles is about 10% greater than the bond strength of the adhesive associated with the first set of articles. The bond strength of the adhesive associated with the third set of articles is about 10% greater than the bond strength of the adhesive associated with the first set of articles, and the bond strength of the adhesive associated with the fourth set of articles is about 15% greater than the bond strength of the adhesive associated with the first set of articles. Such an assembly may be preferred by some practitioners because the appliances mounted on the lower jaw and the appliances mounted on cuspid, bicuspid and molar teeth tend to unintentionally, spontaneously debond more often than the appliances associated with the remaining teeth. In this paragraph, the bond strengths are computed in stress units such as megapascals.

In another embodiment, the tack of the adhesive of the articles of the first set is greater than the tack of the adhesive of the articles of the second set. The increase in tack for the posterior appliances in beneficial in that a greater resistance to sliding movement is provided before the adhesive has hardened. During bonding, the facial surfaces of the posterior teeth are often more vertical than the surfaces of the anterior teeth, and additionally are subject to a greater amount of moisture than the surfaces of the anterior teeth. The increased tack helps to ensure that the posterior appliances remain in place until such time as the adhesive has hardened.

Figures 6, 7, 8:
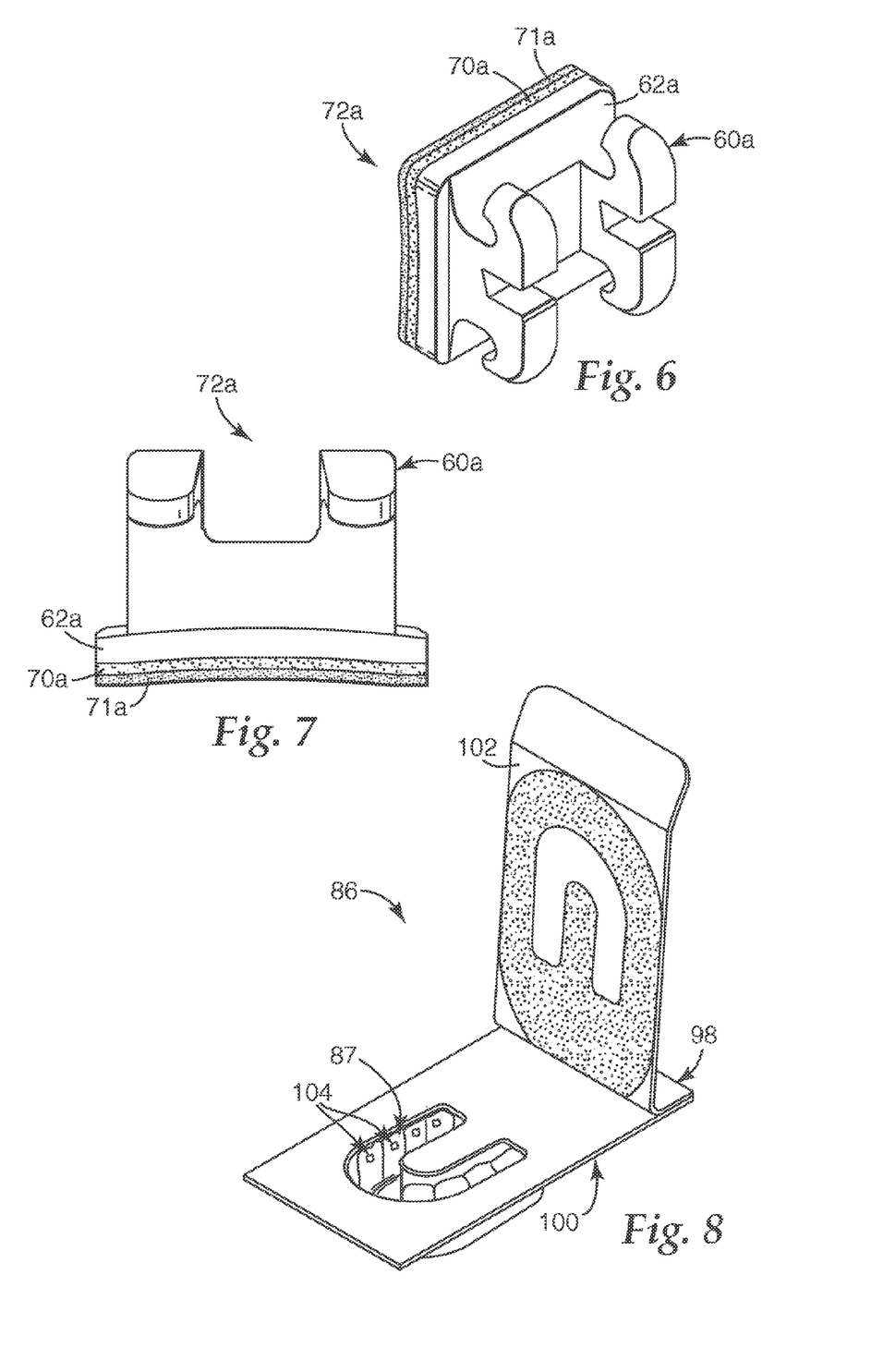
FIG. 6 is an enlarged perspective view of an orthodontic appliance and an adhesive somewhat similar to the appliance and adhesive shown in FIG. 3, except that the adhesive in FIG. 6 is comprised of two layers.
FIG. 7 is a side elevational view of the appliance and adhesive shown in FIG. 6.
FIG. 8 is a perspective view of a packaged orthodontic assembly according to another embodiment of the invention, wherein the assembly includes a placement device for use in indirect bonding techniques.

In another embodiment of the invention, the assembly includes a first set and a second set of articles, and the adhesive of the first set of articles has a greater number of layers than the adhesive of the second set of articles. For instance, the first set of articles may have an adhesive with two layers while the adhesive of the second set of articles may have a single layer. In FIGS. 6 and 7, an exemplary appliance 60a has a first adhesive layer 70a and a second adhesive layer 71a. The adhesive layer 70a of article 72a extends across the base 62a, and adhesive layer 71a extends across adhesive layer 70a. Layers 70a, 71a are layers of different adhesive that may or may not cover the same area. Layers 70a and 71a may independently be discontinuous (e.g., a patterned layer) or continuous (e.g., non-patterned) material extending across all or a portion of a material.

Adhesive layers 70a, 71a may differ in properties including, for example, chemical composition, viscosity, hydrophilicity as disclosed, for example, in U.S. Pat. No. 6,126,922 (Rozzi et al), thickness, curing times, curing mechanisms, color, change in color upon curing, enzyme release, fluoride release, bond strengths upon curing, filler loading, filler types and PH as disclosed, for example, in PCT International Publication No. WO00/69393 (Brennan et al.). Optionally, the layer 70a in contact with the base 62a has a composition that is tailored to enhance the bond between the base 12a and the outer adhesive layer 71a. In that instance, the adhesive layer 70a may vary in composition in accordance with the composition or structure of the base 62a, or in accordance with the composition of the layer 71a.

Additional aspects of multi-layer adhesives for orthodontic appliances, including other alternative constructions, are set out in applicant's co-pending application publication no. 2005/0136370-A1 entitled "MULTI-LAYER ADHESIVES AND METHODS FOR BONDING ORTHODONTIC APPLIANCES TO TOOTH STRUCTURE".

In some embodiments of the present invention, an adhesive delivery system is provided that includes two or more discrete quantities of adhesive extending across at least a portion of an adhesive transfer area of a substrate. At least two of the adhesive quantities vary in composition and/or properties. The substrate is provided as a packaged article. After removing the substrate having the adhesive thereon from the package, if present, one of the quantities of adhesive may be transferred to the base of an orthodontic appliance, which can then be bonded to a tooth structure either through direct or indirect methods. Exemplary adhesive delivery systems are described, for example, in U.S. Pat. No. 6,213,767 (Dixon et al.).

Figure 9:
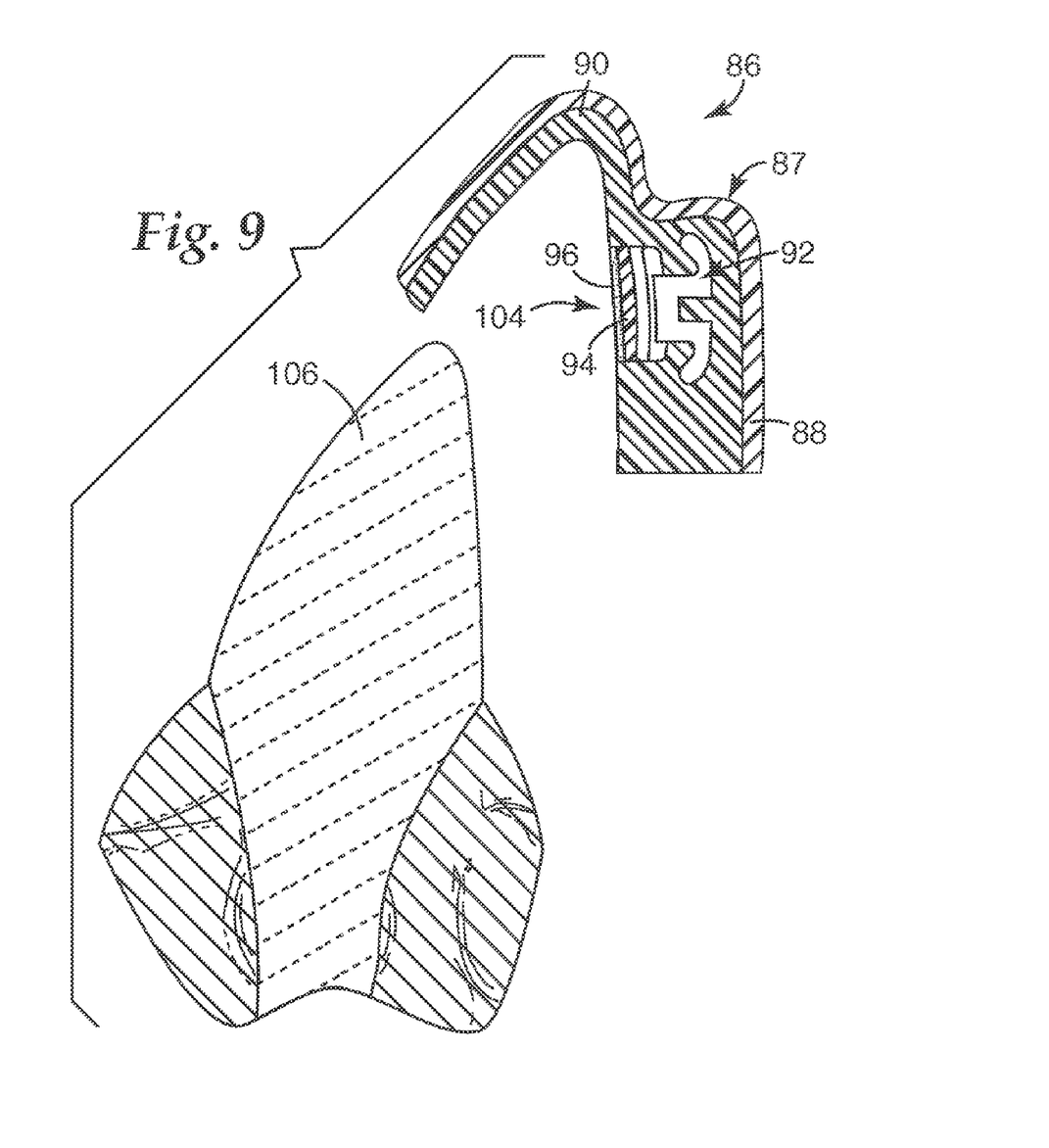
FIG. 9 is an enlarged cross-sectional view of the placement device alone that is depicted in FIG. 8, additionally illustrating the act of applying an appliance to a patient's tooth using the placement device.

A packaged orthodontic assembly 86 according to another embodiment of the invention is shown in FIGS. 8 and 9, and relates to an assembly especially useful for indirect bonding methods. For indirect bonding methods, orthodontic appliances are removed from the package and placed, for example, on a replica plaster or "stone" model of the patient's dental arch to provide a custom base for later mounting on the patient's tooth structure, commonly using a placement device. In one embodiment, the orthodontic appliances have an adhesive on the bases thereof to bond to the replica plaster or "stone" model, to provide the custom base. Exemplary indirect bonding methods are described, for example, in co-pending U.S. Pat. Publication No. 2005/0074716.

The orthodontic appliance provided in the placement device may have a single layer or multi-layer adhesives on the custom bases (or alternatively non-custom bases) for bonding to the patient's teeth. Referring to FIG. 9, the placement device 87 (comprising shell 88, matrix material 90, and appliances 92) is shown in cross-sectional view. The appliances 92 preferably include custom bases 94 that are coated with an adhesive 96. The placement device 86 is then placed in a package 98 (FIG. 8) by the manufacturer and shipped to the practitioner's office.

The package 98 includes a container 100 and a cover 102 that is releasably connected to the container 100. Preferably, the package 98 is similar to the package 74, in that the package 98 protects the adhesive 96 from light, moisture and contaminates. Additional aspects and alternatives for the package 98 are set out in applicant's co-pending U.S. Patent Publication No. 2005/0074716 and entitled "Apparatus for Indirect Bonding of Orthodontic Appliances and Method of Making the Same" and Publication No. 2005/0074717 entitled "Method and Apparatus for Bonding Orthodontic Appliances to Teeth".

In the embodiment shown in FIGS. 8 and 9, each of the appliances 92 and the associated adhesive 96 together present an article 104. Advantageously, the assembly 86 comprises two or more articles 104, and at least one article 104 includes an adhesive 96 that varies from the adhesive 96 of at least one other article 104. As a consequence, the composition, characteristics or properties of the adhesive 96 may be varied in accordance with the type of appliance 92 associated with the adhesive 96, or with the intended location of the appliance 92 and the adhesive 96 in the patient's oral cavity. Optionally, the custom bases 94 may also vary in composition and/or properties from one appliance to the next.

The variation in the adhesive 96 may be carried out by one or more of the methods described above in connection with the assembly 80.

Once the patient has returned to the office, the bonding procedure is undertaken. Preferably, any tooth preparation steps are carried out before the packaged placement device 87 is opened. In this manner, the adhesive 96 is not unduly exposed to ambient light or air. After any tooth preparation steps are completed, the container 98 is opened and placement device 86 is removed from the package.

The shell 88 is then positioned over the corresponding teeth and seated, optionally with a swinging, hinge-type motion. In FIG. 9, the patient's tooth is designated by the numeral 106. Since the shape of the cavity of the matrix material 90 matches the shape of the underlying teeth, the appliances 92 are simultaneously seated against the underlying teeth 106 at precisely the same locations corresponding to the previous position of the appliances 92 on the replica. Preferably, pressure is then applied to the occlusal, labial and buccal surfaces of the shell 88 until such time as the adhesive 96 has sufficiently hardened. Optionally, finger pressure may be used to firmly press the appliances 92 against the enamel surfaces of the patient's teeth 106.

Once the adhesive 96 has hardened, the shell 88 is carefully removed from the patient's dental arch. Preferably, the shell 88 is first separated from the matrix material 90, which remains in place over the dental arch along with the appliances 92. Next, the matrix material 90 is detached from the appliances 92. Optionally, a hand instrument such as a scaler may be used to help hold each appliance 92 against the surface of the respective tooth 106 of the patient as the matrix material 90 is peeled away from the appliances 92. However, in instances where a relatively soft matrix material is employed or otherwise readily releases from the appliances 92, the use of a scaler to help avoid fracturing the fresh adhesive bond is optional. As another option, the shell 88 may be separated from the matrix material 90 before the adhesive 96 has hardened. This option is particularly useful when the adhesive 96 includes a light-curable adhesive. Once the matrix material 90 has been detached from the appliances 92, an archwire is placed in the slots of the appliances 92 and ligated in place.

Color Test

Quantification of initial and bleached color of adhesive samples is performed with a portable ultraviolet-visible (UV-Vis) spectrometer available under the trade designation EPP2000C from StellarNet, Inc. (Oldsmar, Fla.) equipped with a 400-micron fiber reflectance probe and calorimeter software available under the trade designation SpectraWiz CIELAB from StellarNet, Inc. (Oldsmar, Fla.).

To prepare samples for color measurement, an adhesive sample is extruded onto a polyester release liner, a metal ring is placed around the adhesive, and a second release liner is placed on top of the adhesive. The resulting construction is then pressed between two Plexiglas plates with the metal ring controlling the adhesive thickness to 0.51 mm. With the light source of the spectrometer switched off, the adhesive sample between the two release liners is placed on top of a white reflectance standard (Part No. RS50, 50-millimeter diameter, Halon type >97% reflectance, 300-1500 nanometers, StellarNet, Inc.). The fiber optic probe of the spectrometer is positioned 6.3 millimeters above the sample at a 45° angle. Color measurements are taken through the top release liner at an exposure time of 1000 milliseconds and with the center of the adhesive under the beam. The software captures the reflectance spectrum and converts the input to $L^*$, $a^*$ and $b^*$ values. The $a^*$ value is indicative of the redness of the sample with higher numbers indicative of greater redness.

Cured adhesive samples are prepared in the same manner described herein, except that the adhesive pressed between the two polyester release liners is cured for 3 minutes in a light curing oven available under the trade designation TRIAD 2000 from Dentsply International, Inc. (York, Pa.). The cured adhesive sample with the polyester liners intact is placed directly onto the white reflectance standard. The light source of the spectrometer is switched on and $L^*$, $a^*$ and $b^*$ values are measured as described herein with each reported value representing the average of 3 measurements.

The complete disclosure of all patents and patent applications cited herein are incorporated by reference. The foregoing detailed description and examples have been given for clarity of understanding only. No unnecessary limitations are to be understood therefrom. The invention is not limited to the exact details shown and described, for variations obvious to ones skilled in the art will be included within the invention defined by the claims.

The invention claimed is:

1. An orthodontic assembly comprising a first set of articles and a second set of articles, each article of the first and second set including an orthodontic appliance having a base for connection to a tooth of an orthodontic patient and an adhesive contacting and extending across at least a portion of the base of the corresponding appliance, wherein the appliance of each article of the first set is a posterior appliance for posterior teeth of a dental arch, wherein the appliance of each article of the second set is an anterior appliance for anterior teeth of the dental arch, and wherein the adhesive of at least one article of the first set has a hydrophilicity greater than the hydrophilicity of the adhesive of at least one article of the second set.

2. An orthodontic assembly according to claim 1 wherein the adhesive of the articles of the first set has a viscosity that is less than the viscosity of the adhesive of the articles of the second set.

3. An orthodontic assembly according to claim 1 wherein the adhesive of the articles of the first set provides a bond strength that is greater than the bond strength provided by the adhesive of the articles of the second set.

4. An orthodontic assembly comprising a first set of articles and a second set of articles, each article of the first and second set including an orthodontic appliance having a base for connection to a tooth of an orthodontic patient and an adhesive contacting and extending across at least a portion of the base of the corresponding appliance, wherein the appliance of each article of the first set is a lower appliance for the teeth of a lower jaw, wherein the appliance of each article of the second set is an upper appliance for the teeth of the upper jaw, and wherein the adhesive of at least one article of the first set has a hydrophilicity greater than the hydrophilicity of the adhesive of at least one article of the second set.

5. An orthodontic assembly according to claim 1 or 4 wherein the assembly comprises at least two packages, and wherein each package receives one of the articles of the respective set.

6. An orthodontic assembly according to claim 5 wherein the assembly includes a holder having a plurality of receptacles, and wherein said each package is received in a respective one of the receptacles.

7. An orthodontic assembly according to claim 6 wherein the packages are removably received in the receptacles.

8. An orthodontic assembly according to claim 1 or 4 wherein the adhesive of at least one article is a light-curable adhesive, and wherein the assembly comprises at least one package that comprises a material that blocks the passage of actinic radiation.

* * * * *

UNITED STATES PATENT AND TRADEMARK OFFICE
CERTIFICATE OF CORRECTION

| | |
|---|---|
| PATENT NO. | : 7,910,632 B2 |
| APPLICATION NO. | : 11/422790 |
| DATED | : March 22, 2011 |
| INVENTOR(S) | : David K. Cinader, Jr. |

It is certified that error appears in the above-identified patent and that said Letters Patent is hereby corrected as shown below:

Column 14
Line 11, Delete "calorimeter" and insert -- colorimeter --, therefor.

Signed and Sealed this
Tenth Day of May, 2011

David J. Kappos
*Director of the United States Patent and Trademark Office*